United States Patent
Fucile et al.

(10) Patent No.: US 9,395,338 B2
(45) Date of Patent: Jul. 19, 2016

(54) SENSOR SYSTEM FOR ENVIRONMENTAL IMPACT MONITORING

(71) Applicant: Woods Hole Oceanographic Institution, Woods Hole, MA (US)

(72) Inventors: Paul Dominic Fucile, Waquoit, MA (US); Glenn Elwin McDonald, Marston Mills, MA (US); Edward Leo Hobart, Cataumet, MA (US)

(73) Assignee: Woods Hole Oceanographic' Institution, Woods Hole, MA (US)

( * ) Notice: Subject to any disclaimer, the term of this patent is extended or adjusted under 35 U.S.C. 154(b) by 7 days.

(21) Appl. No.: 14/534,386

(22) Filed: Nov. 6, 2014

(65) Prior Publication Data

US 2015/0131084 A1    May 14, 2015

Related U.S. Application Data

(60) Provisional application No. 62/037,487, filed on Aug. 14, 2014, provisional application No. 61/903,162, filed on Nov. 12, 2013.

(51) Int. Cl.
*G01N 21/00* (2006.01)
*G01J 1/00* (2006.01)
(Continued)

(52) U.S. Cl.
CPC .............. *G01N 29/14* (2013.01); *F03D 17/00* (2016.05); *G01N 29/46* (2013.01); *F05B 2270/333* (2013.01); *F05B 2270/81* (2013.01); *G01N 2291/2693* (2013.01); *Y02E 10/722* (2013.01)

(58) Field of Classification Search
CPC ....... G01N 29/46; G01N 29/14; G01N 29/28; G01N 29/11; G01N 29/40; G01N 2291/2693; G01N 2291/014; G01M 99/00; F03D 11/0091; F05B 2270/333; F05B 2270/81; G05B 19/02; G01V 1/001; F41H 11/12; G01S 15/04; G01S 15/025; G01S 15/88
USPC .............. 356/72, 213; 250/573, 239; 73/627; 367/87
See application file for complete search history.

(56) References Cited

U.S. PATENT DOCUMENTS 5,808,969 A * 9/1998 Arnaud .................... G01V 1/00
                                                  367/103
5,974,881 A * 11/1999 Donskoy ................ G01N 29/11
                                                  367/87

(Continued)

FOREIGN PATENT DOCUMENTS

DE      102011117239.8    * 10/2011    ............... G07D 7/08
WO     WO-2013-017646 A1   2/2013

(Continued)

OTHER PUBLICATIONS

"Sentinel: An Integrated Wind Turbine Acoustic Noise and Shadow-Flicker Detection and Mitigation System", FAQ Handout Rev. 10.29.13, 2013, pp. 1-7, Associated Wind Developers, Plymouth, MA, USA.

(Continued)

*Primary Examiner* — Tarifur Chowdhury
*Assistant Examiner* — Sunghee Y Gray
(74) *Attorney, Agent, or Firm* — Douglas Denninger (57) ABSTRACT

A self-contained monitor array for measuring at least one type of electromagnetic emission and at least one type of mechanical wave emission from a marine-based and/or terrestrial human activity or installation such as alternate energy sources. A multi-modal monitor system includes at least two such arrays, at least one clock, and at least one data storage unit.

12 Claims, 6 Drawing Sheets

(51) Int. Cl.
*G01N 9/24* (2006.01)
*G01S 15/00* (2006.01)
*G01N 29/14* (2006.01)
*G01N 29/46* (2006.01)

(56) References Cited

U.S. PATENT DOCUMENTS

| | | | | |
|---|---|---|---|---|
| 6,415,666 | B1* | 7/2002 | Donskoy | F41H 11/12 367/87 |
| 8,151,644 | B2* | 4/2012 | Brandt | G01H 9/00 73/643 |
| 2007/0234730 | A1* | 10/2007 | Markham | G01N 21/359 60/772 |
| 2011/0204629 | A1 | 8/2011 | Sorensen et al. | |
| 2011/0273704 | A1 | 11/2011 | Burba | |
| 2014/0193257 | A1 | 7/2014 | Ormei et al. | |
| 2014/0290367 | A1* | 10/2014 | Domke | G01N 29/11 73/596 |

FOREIGN PATENT DOCUMENTS

WO WO-2013-017648 A2 2/2013
WO WO-2013-017648 A3 2/2013

OTHER PUBLICATIONS

"Introducing: The Wind Turbine SENTINELTM", Oct. 29, 2013, p. 1, Associated Wind Developers, Plymouth, MA, USA.

* cited by examiner

SENSOR SYSTEM FOR ENVIRONMENTAL IMPACT MONITORING

CROSS-REFERENCE TO RELATED APPLICATION

This application claims priority to U.S. Provisional Application No. 61/903,162 filed 12 Nov. 2013 and to U.S. Provisional Application No. 62/037,487 filed 14 Aug. 2014.

FIELD OF THE INVENTION

This invention relates to measurement of emissions from selected sites and more particularly to multi-modal monitoring of such emissions.

BACKGROUND OF THE INVENTION

Continuous quantitative monitoring of sound, light, vibration and/or EM fields is critical for evaluating the environmental impact of a wide variety of mechanical installations. Currently available monitoring systems tend to be uni-modal, often hand held and weather-intolerant and are not useful for taking persistent, calibrated, time-stamped readings across multiple modalities. The inventive multi-modal environmental monitor described herein is easy to use, low in cost and portable for continuous and simultaneous quantitative monitoring of three or four modalities at a single installation. The invention facilitates the comparison of impact as occurs in response to discrete environmental fluctuations, and/or to coordinately monitor trends over time. Typical installations of the inventive devices include, terrestrial and marine based windmills, hydrokinetic turbines as well as a wide variety of transportation-related (eg airports) and industrial installations.

Wind and aquatic hydrokinetic energy sources (e.g. turbines) while considered 'green' still have environmental impacts. A wind turbine generates acoustic noise, shadow flicker, an EM field, and a measurable amount of ground vibration. Similarly, aquatic hydrokinetic systems produce an acoustic signal and may cause light field modifications, and in some instances, ground vibrations. When sited appropriately, these energy sources are capable of operating with no detrimental effect to the environment. The largest hurdle to overcome for some proposed installations may involve complying with regulatory agency mandates rather than those of a technical nature. Determining this impact is a necessary requirement for developers, municipalities, and end users.

Shadow or flicker measurement and/or control is discussed by Sorensen et al. in US Patent Publication No. 2011/0204629 and by Acosta et al. in WO2013/017646 and WO2013/017648. Shaded and exposed radiation sensors are disclosed by Barba in US Patent Publication No. 2011/0273704. An acoustic noise monitoring system for a wind turbine is described by Ormel et al. in WO2013/023660.

Performance optimization services for wind turbines are provided by companies such as Upwind Solutions, currently having a website at "www.upwindsolutions.com". One product currently offered is the UpWind Sentinel™ Drivetrain Health Monitoring solution that allegedly provides multi-source data acquisition including vibration sensing using a plurality of MEMS accelerometers.

Quantifying the potential impact of noise generating and light-level impacting mechanical installations is a necessary requirement for both regulatory bodies, developers and end users. Still, commercially available technology for these measurements employ weather-intolerant instrumentation and, in some cases, inadequate sensors, making long-term time series assessments (e.g., weeks, months or years) impossible. The implementation of uniform and traceable monitoring protocols without standardized instruments often makes subsequent analyses difficult, confusing, or even unusable.

In addition, because the impact of a mechanical installation on the local environment may vary over time and weather conditions, smart control of a mechanical installation performance based on prevailing noise, vibrations or light conditions may often be desirable.

Therefore, there is a need for a readily-available, easily installable, low-maintenance, and durable sensor package, and systems having two or more of such sensor packages, for the production of reliable standardized uniform data set to help facilitate the development and smart electronic control of alternate energy production installations.

SUMMARY OF THE INVENTION

This invention features a self-contained and economical system that repeatably and consistently measures at least one type of electromagnetic emission, such as optical radiation or narrow-band EM field, and at least one type of mechanical wave emission, such as ground-coupled vibration or low-frequency (infrasonic) acoustic emissions, for marine-based and/or terrestrial alternate-energy sources or other installations or human activity.

This invention also features a multi-modal monitor system to obtain quantitative, coordinated measurement of emissions from a designated outdoor source. The monitor system has at least two sensor arrays, each array including a first sensor for measuring at least one type of electromagnetic emission and generating a first emission signal, and a second sensor for measuring at least one type of mechanical wave emission and generating a second emission signal. The first and second sensors are contained within a master housing capable of being placed operationally in an outdoor location to be monitored. The system further includes at least one clock to synchronize the first and second emission signals from each array, and at least one data storage unit capable of storing the first and second emission signals from each array over time.

In some embodiments of either or both of the terrestrial and/or marine systems, the monitor further includes a controller which compares the emission signals of the designated outdoor source with pre-determined ranges of acceptable values and alters the performance of the designated outdoor source when at least one parameter deviates from the pre-determined range of acceptable values for at least a specified period of time.

DEFINITIONS

Degree-restricted radiance aperture sensing geometry: Limiting the optical viewing angle to a relatively narrow viewing cone, such as a viewing angle of 5-15 degrees, more preferably about 10 degrees.

Acoustic Reflector: The acoustic reflector improves the weather tolerance for what is normally a non-weather tolerant component. The acoustic sensor is positioned within a weather-protected region of the device housing. The reflector is positioned in an orientation which directs the acoustic signal to be measured to the acoustic sensor. In one embodiment, the reflector comprises a downward slanted non-compliant surface that reflects horizontally directed acoustic waves in an upward direction towards a receiving microphone element.

Direct radiative measurements: In this invention relates to electromagnetic radiation, especially optical signals, that arrive at one or more sensors selected to detect the desired type of electromagnetic radiation, such as at least one optical sensor in a straight undisturbed path (e.g. less than 180 degree, a spherical measurement describes accepting radiation from all directions $2\pi$).

Flicker: In this application refers to the stroboscopic effect that occurs when a wind turbine or hydrokinetic rotor passes between the sun and the receiving location, causing a recurrent shadow at the sensor.

Reference Light: Refers to source unrestricted light field. In the case of the wind turbine applications, this is the undisturbed light measured slightly off-axis from the direction of the turbine in a region absent of Flicker. For marine applications, this is the ambient light reaching the sensor from the water column.

Pressure Distribution Manifold: When making infrasonic (less than 20 Hz) measurements by use of a micro-barometer in locations where wind velocity is experienced, it is desirable to distribute the pressure intake port by using an array of openings to reduce error attributed to the Bernoulli effect.

Undisturbed light field: Describes a free field where light is not modified either by reflection or adsorption.

Spherical measurements: Unlike radiative measurements which generally describe a viewing cone of less than 180 degree, a spherical measurement describes accepting radiation from all directions ($4\pi$) that are received on the surface of a sphere.

Weather-tolerant: Describes the ability for a component to operate or survive the elements including but not limited to sun, rain, snow, wind, heat, cold conditions, and dust. Some components may be enclosed to work under adverse conditions while others may survive to work at a later time.

DETAILED DESCRIPTION OF THE PRESENTLY PREFERRED EMBODIMENTS

In preferred constructions, the invention is implemented as a fully-integrated solid state sensor package for temporary or permanent field installation. It is designed for the simultaneous and continuous measurement of narrow band EM field, ground-coupled vibration, optical, and low frequency (infrasonic) acoustic emissions. The invention provides for onboard data storage, digital output, and networking capability. Data is recorded in a uniform and traceable monitoring protocol for the production of a reliable standardized data set. The invention may be used to control the performance of equipment or machinery that generate signals to be monitored by the sensing capabilities of the invention This invention may be accomplished by at least one sensor package which monitors at least one type of electromagnetic radiation and at least one type of mechanical wave emission. In another aspect of the invention, at least two sensor packages are deployed in a monitoring system. In yet another aspect, a system has at least one such multi-modal sensor package and a controller that alters a source of the emissions to minimize undesirable emissions and enhance compliance with monitoring requirements.

Possible sources of emissions to be monitored include Wind and Hydrokinetic turbine installations. As illustrated in FIGS. 1A-1B and 5A-5B and described below, sensor packages according to the present invention preferably employ an integrated sensor array for the measurement of mechanical, optical, and electrical emissions that are produced in the vicinity of the installations. The invention may also be applied more broadly than these specific fields of use and may also be used to monitor human activity such as highway noise, and headlight impact as well as having the potential to be scaled for industrial or scientific applications.

By providing a calibrate-able, easily installed, weather-tolerant, low maintenance, and simple-to-operate sensor package, a reliable, uniform data set can be produced to help facilitate the development and/or monitoring of alternate energy production installations. Quantifying this potential impact is a necessary requirement for both developers and end users. Preferred sampling periods run from 1 to 24 hours to several weeks, or several months or more. In some embodiments sampling occurs on an ongoing basis for years or even indefinitely.

Figure 1A:
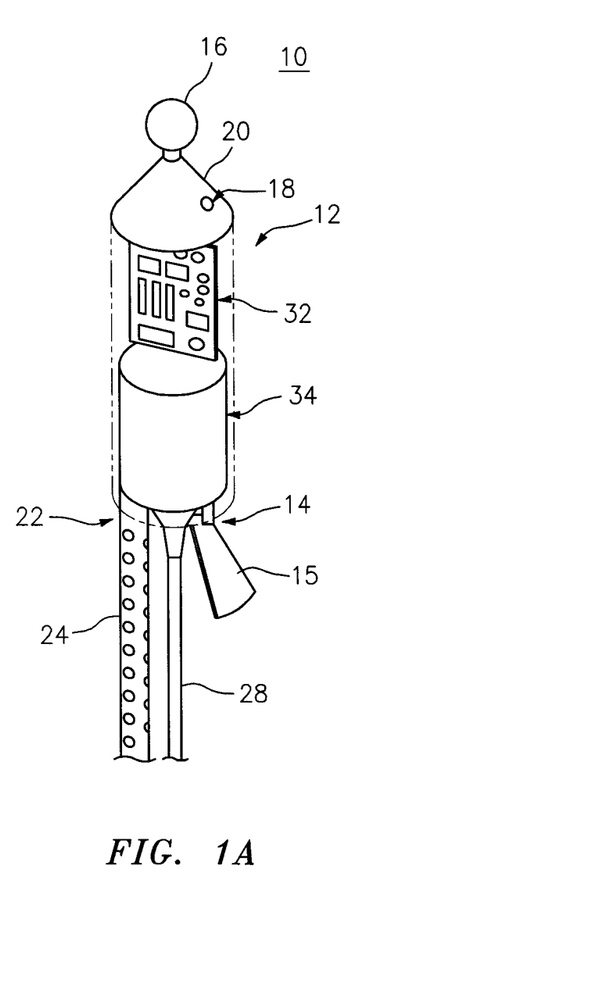
FIG. 1A is a schematic perspective view of the upper portion of a multi-modal environmental monitor according to the present invention for terrestrial sites such as a wind turbine installation.
Figure 1B:
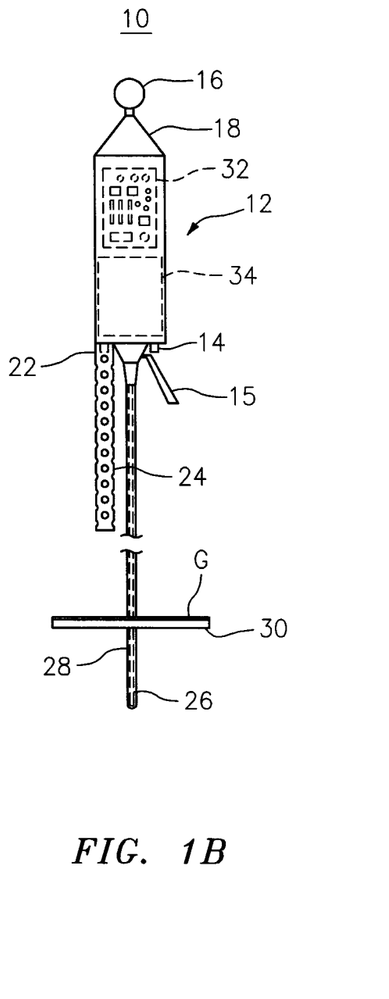
FIG. 1B is a schematic side view of the monitor of FIG. 1A.

In one construction as illustrated in FIGS. 1A and 1B, the major components of the monitor or sensor array 10 are: a housing 12, an acoustic sensor 14 such as a microphone positioned relative to an acoustic reflector 15, and at least one optical sensor such as a $4\pi$ steradian scalar collector 16, a $2\pi$·irradiance collector 18 mounted in a cone 20, and an off-axis optical radiation collector (not visible). In this construction, monitor 10 further includes an infrasonic sensor 22 with a wind-masking acoustic manifold 24, and a vibration sensor 26 such as an accelerometer mounted on support post 28 below stabilization plate 30 which preferably is installed slightly below ground level G. Sensor array 10 preferably also includes processing electronics 32 and an internal power source 34 within housing 12. An embedded temperature sensor (not visible) is provided in certain constructions to indicate that the monitor 10 is operating within normal parameters.

In one construction, housing 12 has a height of approximately 40 cm and a diameter of 10 cm. Typically, housing 12 is positioned approximately two meters above ground G. In another construction, the housing 12 is approximately 10 inches tall, 3 inches in diameter, and is positioned approximately 1.5 meters above ground G. In one construction, power source 34 includes rechargeable 7.2V Li—Po batteries which provide 3-5 weeks of operation; in other constructions, a 12V/100 mA power supply or Power Over Ethernet is provided. Weather-tolerant materials and construction allow the device to operate under severe conditions. Both marine and terrestrial units may employ the same processors and data acquisition electronics core.

The sensors for both applications shown were selected to resolve low frequency (ground-coupled or infrasonic) through mid-frequency (acoustic) mechanical wave emissions and optical (flicker) emissions as compared to general light field signals. The optical sensor preferably has a wide dynamic range and operates even in direct sunlight. Low-frequency, ground-induced vibrations are sensed by an accelerometer (e.g. 3 axis accelerometer) mounted in the base of the mounting pole or internally when installed on the more massive bottom mount. The processor, data storage, and communication components are low power to extend battery life. The internal acquisition parameters can also be remotely modified.

Typical field operation time for the device is 30 to 60 days without the need to change batteries or download data. In locations where power and communications are available, operation can be indefinite.

Components of the Terrestrial Unit

Acoustic Sensor:

The instant invention employs weather-tolerant acoustic sensors and that meet or exceed the sensitivity required to measure the desired signal, typically from 20 Hz to 22,000 Hz to enable ⅓ Octave spectrum analysis. Weather tolerance is accomplished by configuring the acoustic sensor with an acoustic reflector to allow the sensor to be protected by positioning within the device housing out of direct contact with weather elements. Generally speaking, the acoustic reflector is fabricated from any materials which provide mechanical stability and an acceptable minimal level of absorption of acoustic energy. In some embodiments little or no acoustic energy is absorbed by the acoustic reflector.

Specific examples of materials suitable for fabrication of the acoustic reflector include: sheet aluminum, stainless steel, common iron, carbon fiber, fiberglass, and durable plastics Infrasound Sensor:

In most embodiments the invention comprises an infrasound sensor. Infrasound sensors may use any means to measure infrasound including pressure difference detectors and velocity microphones. Preferred sensors measure infrasound below 20 Hz. In one embodiment the sensor incorporates an element to reduce wind effects attributed to the Bernoulli effect over the primary pressure sensing port. An element to reduce wind effects in the signal such as a pressure distribution manifold is also incorporated onto the device (e.g. mounted below the sensor).

In the preferred embodiment, a time-adjusted ambient average pressure reservoir approach to monitoring infrasound is employed to provide barometric compensation by the use a dual port differential micro-barometer. Other strategies for the measurement of infrasonic signals consistent with the invention include the use of a large capacitive area diaphragm. Although conventional velocity microphones may be employed, their inability to measure ambient average pressure differences below 20 Hz make them less desirable and in many instances unusable.

Pressure transducers for the measurement of infrasound are selected to have as broad a detection range as possible as the signal can span both a dynamic range and frequency response of many decades above ambient barometric shift (up to 40 Hz), a sensitivity capable of resolving +/−2 milli Pascal are useful, preferred embodiments will have the ability to measure up to a range of +/−4 Pascal to insure linear operation over the entire dynamic range, and on the order of 2, 3, 4, preferably 5 or greater decades above ambient barometric shift.

Ground Vibration Sensor:

Low frequency, ground-induced vibrations are sensed by a 3-axis accelerometer MEMS (Micro Electro-Mechanical System) or voice coil sensor mounted in the base of the mounting pole.

Flicker Sensor:

The optical sensors for the measurement of blade or hydrokinetic rotor flicker are mounted to provide both spherical and direct radiative measurements. Also in many embodiments, incorporated into the output is an integration of slightly off axis undisturbed ambient light level to provide a reference for the approximate driving signal (e.g. unperturbed solar signal).

The optical sensor(s) for the detection of flicker have the capability of measuring one or more of a.) source or ambient light, b.) light changes indicative of flicker and c.) integration to provide a value for the undisturbed light field.

The optical sensors for the detection of flicker are configured within a device so that they may receive a direct input of the flickering environmental light to be measured. In some less preferred embodiments, it may be advantageous to direct some or all of the sensors towards a reflective surface within the device or the environment which is considered to be indicative of the flickering environmental light.

In some embodiments the optical sensor preferably has a linear response over a wide dynamic range to allow sensing of small signals under low light. Specifically, a three-channel optical sensor has a wide dynamic range and will operate in linearly from sunrise conditions to direct sunlight. It provides a 4 pi steradian scalar (spherical collector) and a directed 10 degree restricted radiance aperture sensing geometry mounted in the primary housing to give an indication of the resulting direct and local light field changes due to blade induced flicker. The third optical channel is generally mounted at a lower portion of the support and is directed off-axis from the direction of the turbine to provide an integrated light value of the undisturbed light field. The data obtained is used to describe the resulting local effect of a flicker event.

An alternative embodiment employs an optical sensor that senses a change in reflection off the interior of the drum. This feature enhances the capability of the device to obtain optical signals even in severe weather conditions. Each of the embodiments as described generally requires a mechanical vent hole.

EM Field Detection:

EM field detection is an optional capability of the device which may be installed within the device housing along with the other sensor apparatus or in some embodiments EM detection will integrate into the sensor package by a remote cable. Typically, EM field is measured from steady state to at least 60, 80, 100 or preferably 120 Hz or more.

Common Components: Housing, Clock, Output Integration & Signal Analysis

Device Housing:

The device and related sensor housing are designed to withstand continuous operation over an intended range of −20, −10, or −5 Degrees F to +110 degrees F. The housing materials are selected to withstand operation in direct sunlight with material breakdown. Suitable materials include plastics, stainless, steel, clear acrylic, glass, and other non-reactive and/or environmentally stable materials.

Electronics Package:

The processor, data storage, and communication electronics are selected for low power operation to extend battery life. The internal acquisition program can be remotely modified when sampling resource allocation is required. Data are recorded internally or are available for real-time transmission. The data set produced includes a time stamp followed by values for each sensor, with time being counted by at least one clock. The unit typically operates for 10, 20 or 30 days or longer without the need to change batteries or download data. Units intended for subsurface operation can be configured to operate for up to 6 months as oceanographic instrumentation often have limited access due to ship scheduling. In locations where power and communications (Ethernet) are available, unattended operation can be indefinite Since a site typically may require multiple sensors, the requirement to synchronize measurements is addressed by using a temperature compensated clock.

Power consumption in most embodiments is low though the primary (battery) power source can be supplemented by a modest (5 W) solar panel or other convenient energy sources.

Device Calibration:

Fundamental to this invention is the ability to perform calibrations of the entire sensor suite both prior, during, and post deployment. The design provides specific solutions that do not require the disassembly thus to allow calibration in the field. Economical reference standards allow the end user to perform calibrations without sending the unit back to the factory. This is often important when performing uninterrupted time series measurements.

Device Design and Sensor Configuration

Generally speaking, all configurations will observe one or more of the following design principles:

1.) The weather hardened sensors shown in FIGS. 1A-1B were selected to resolve low frequency ground coupled and acoustic infrasonic signals, audible acoustic, and optical light field modified (blade induced flicker) signals. While being tolerant to adverse weather, the acoustic sensor assembly is easily field serviceable.

2.) The data are recorded as a synoptic set with the fundamental sampling frequency for low frequency signal (infrasound, seismic, and blade flicker) being set at 40 Hz to satisfy the Nyquist requirement for infrasonic signals. Conventional acoustics are sampled 44.1 KHz to satisfy the Nyquist requirement for 22 KHz signal detection. To reduce data storage requirements, A Fast Fourier Transform (FFT) is applied to recorded data to provide an 11 band, ⅓ octave spectrum data representation.

Components of the Aquatic Applications

Figure 5A:
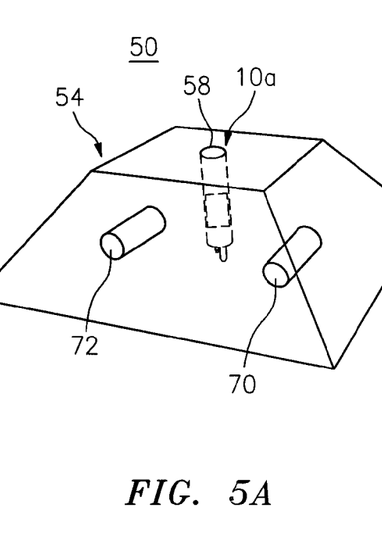
FIG. 5A is a schematic perspective view of a self-contained marine monitor according to the present invention.
Figure 5B:
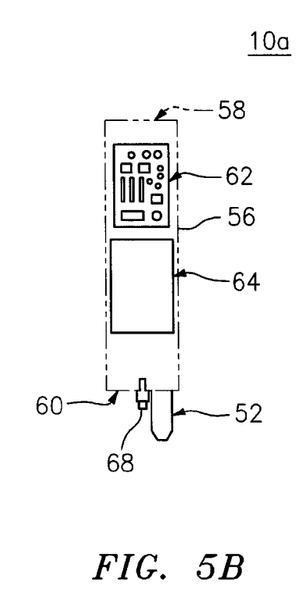
FIG. 5B is an enlarged side view of the sensor package of FIG. 5A.

The aquatic device 50, FIGS. 5A-5B, includes a sensor package 10a which is substantially the same as the terrestrial unit 10, FIGS. 1A-1B, with certain modifications including the following items. For submerged applications, the acoustic sensor or microphone typically is replaced by a wide-band hydrophone 52. The analogous weather-tolerance feature for submerged instrumentation is protection from depth-related pressure, corrosion and biological fouling. This embodiment makes use of best-known oceanographic instrumentation practices to protect the electronics, sensors, and housings from pressure and bio-fouling while extending life between servicing. When deployed along the bottom of a body of water, for example, outer casing 54 preferably is low-profile and snag-resistant to avoid entanglement with trawls and other fishing gear.

The design 50 for marine use, FIGS. 5A-5B, is capable of operating to depths of greater than 5 meters, preferably greater than 10-50 meters and most preferably in excess of 100-300 meters. In this construction, the major components are: the pressure-resistant housing 56, hydrophone 52 as the acoustic sensor, optical sensor 58, wave height (pressure) sensor 60 to measure wave spectra, on-board vibration sensor such as an accelerometer (not visible), processing electronics 62, and an internal power source such as batteries 64. Signal processing algorithms will be used to improve the range of signal-to-noise. The sensor package 10a is mounted to a reinforced frame with an acoustic modem 70, connected or otherwise in communication with telemetry port 68 of sensor package 10a, and an acoustic release 72 in this construction to download data and recover the instrument at a later time.

Other sensor options include at least one thermometer such as a digital thermoprobe to record moment-to-moment external temperature for research and other purposes, and/or GPS to verify precise location of the device, preferably with location stamping and validation of data.

In some embodiments of either or both of the terrestrial and/or marine systems, the monitor further includes a controller which compares the emission signals of the designated outdoor source with pre-determined ranges of acceptable values and alters the performance of the designated outdoor source when at least one parameter falls outside of the pre-determined range of acceptable values (e.g. reaches or exceeds an unacceptable value) for a specified period of time. More specifically, the inventive monitor system controls the performance of an outdoor source in response to one or more emissions from the source selected from the group consisting of EM, shadow, noise, vibration, flicker, and infrasound. In another embodiment the monitor controls the speed of a wind turbine based on impinging flicker from the turbine. Specifically, the monitor signals a reduction in the turbine speed in the presence of unacceptable flicker and/or signals an increase in the turbine speed in the absence of unacceptable flicker. In another embodiment the monitor controls the speed of a wind turbine based on impinging vibration or infrasound caused by the turbine. Specifically, the monitor signals a reduction in the turbine speed in the presence of unacceptable vibration or infrasound and/or signals an increase in the turbine speed in the absence of unacceptable vibration or infrasound. In yet another embodiment the monitor controls the speed of a wind turbine based on impinging noise caused by the turbine. Specifically, the monitor signals a reduction in the turbine speed in the presence of unacceptable noise and/or signals an increase in the turbine speed in the absence of unacceptable noise.

Example 1

Infrasound & Measurements at a Wind Turbine

Figure 2:
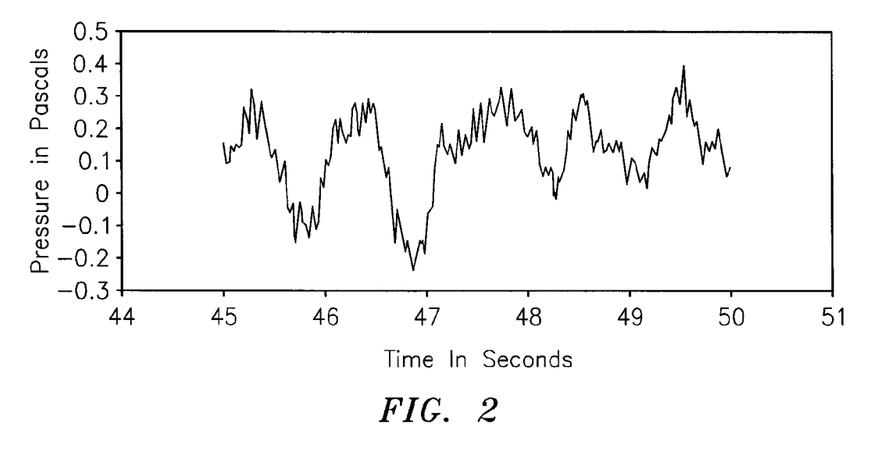
FIG. 2 is a graph of an infrasonic signal showing changes in pressure over time.

FIG. 2 depicts the results of measurements made of infrasound signal showing a 1.3 second blade pass period. The inventive device was placed at a distance of 100 meters from a 1.65 MW Vesta wind turbine.

Instead of the preferred large diaphragm capacitive pressure sensor, the prototype employed in this example utilized a solid state differential pressure transducer similar to those used in medical instrumentation. A custom analog circuit was used to extend the usable range of this device. For the acoustic sensor, a downward-slanted, non-compliant surface was installed to reflect horizontally-directed acoustic waves in an upward direction towards a receiving microphone element.

Example 2

Use of the Sensor Array at a Residence

Figure 3:
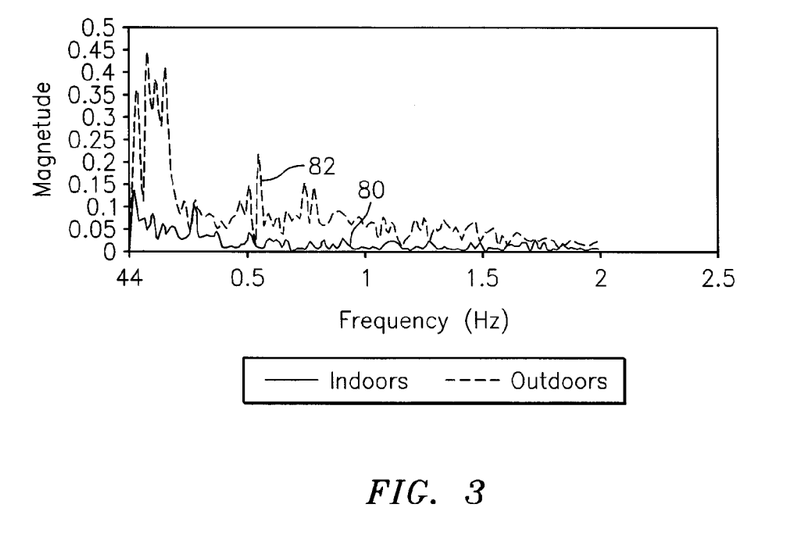
FIG. 3 is a graph of the magnitude of an infrasonic signal frequency spectrum both outside and inside a residence near the source of the signal.

FIG. 3 shows infrasound measurement results from a dual sensor prototype inventive device to measure infrasound both inside, spectrum 80, and outside, spectrum 82, a residence over a frequency range of 0.0 Hz to 2.0 Hz.

Example 3

Use of the Sensor Array to Quantify Flicker Effect

Figure 4:
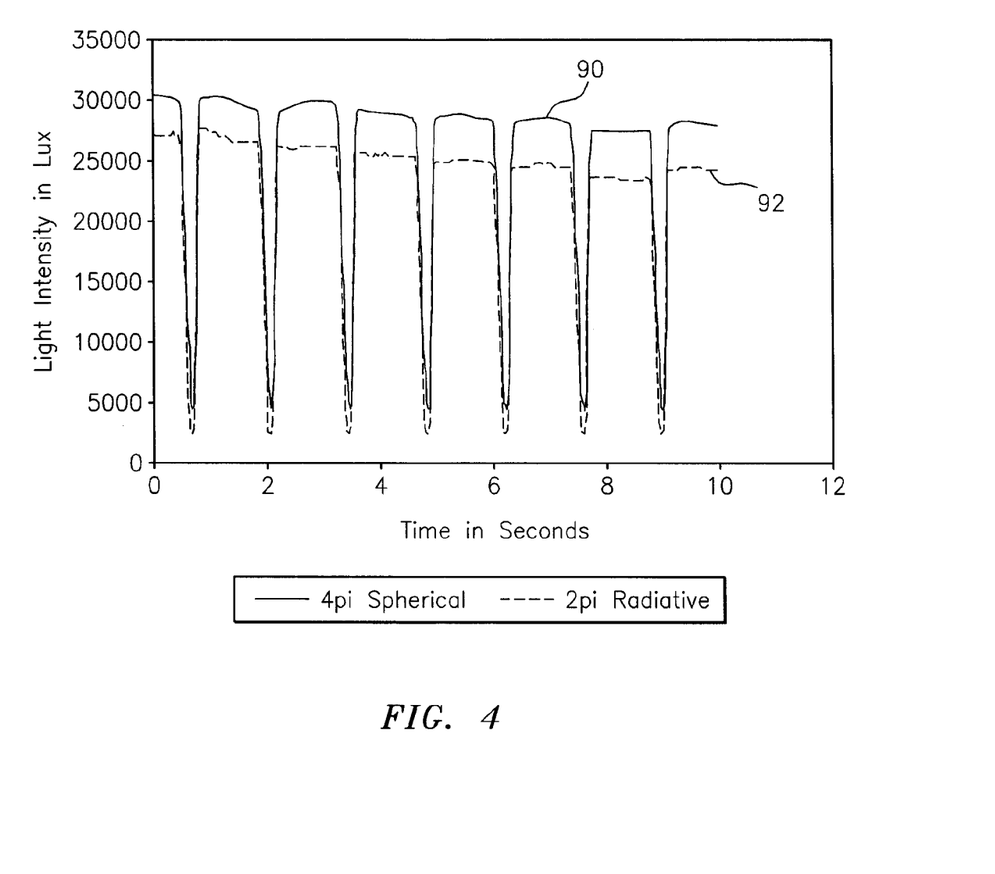
FIG. 4 is a graph of changes in light intensity over time as measured by spherical and radiative sensors.

FIG. 4 shows blade-induced flicker measurement results from a dual sensor prototype inventive device to measure both direct $2\pi$ radiative signal, profile 92, and $4\pi$ spherical collector signal, profile 90.

Figure 6:
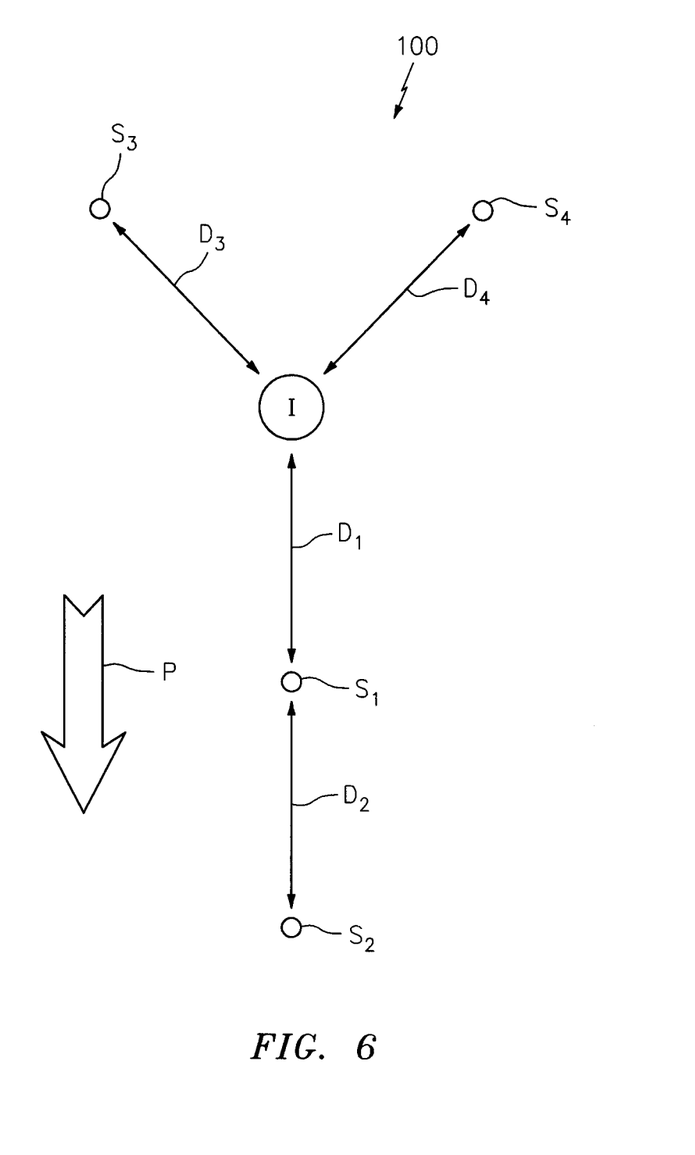
FIG. 6 is a schematic top view of a wind turbine site with four sensor packages deployed in a system according to the present invention.

A monitor system 100 according to the present invention is illustrated in FIG. 6 having four multi-modal sensor units $S_1$, $S_2$, $S_3$ and $S_4$ spaced about installation I, such as a wind turbine, at distance $D_1$ for sensor $S_1$, at distance $D_1+D_2$ for sensor $S_2$, at distance $D_3$ for sensor $S_3$, and at distance $D_4$ for sensor $S_4$, respectively. Each of distances $D_1$-$D_4$ are the same in one construction and, in other constructions, differ from each other. In some constructions, the distances $D_1$-$D_4$ are selected based on the height and/or strength of emissions from installation I. Arrow P represents the direction of flow of a prevailing wind for terrestrial sites and of a prevailing current for underwater sites; typically, sensor $S_1$ will experience the strongest noise effects because it is positioned "downstream" of the prevailing flow. On average over time, upstream sensors $S_3$ and $S_4$ are likely to experience the weakest noise effects from installation I.

When installation I is a wind turbine, sensor $S_1$ preferably experiences at least some flicker effects while sensor $S_2$ is positioned beyond the reach of any flicker effects. In other words, the zone of flicker effects preferably has a distance that is less than the sum of distances $D_1$ and $D_2$. In other constructions, arrow P represents a primary direction of concern for potential flicker effects or other parameter of interest. Sensors $S_3$ and $S_4$ are placed at other locations near installation I to provide complementary sensor readings as desired or to provide information regarding progression of the flicker shadow with movement of the Sun.

Figure 7:
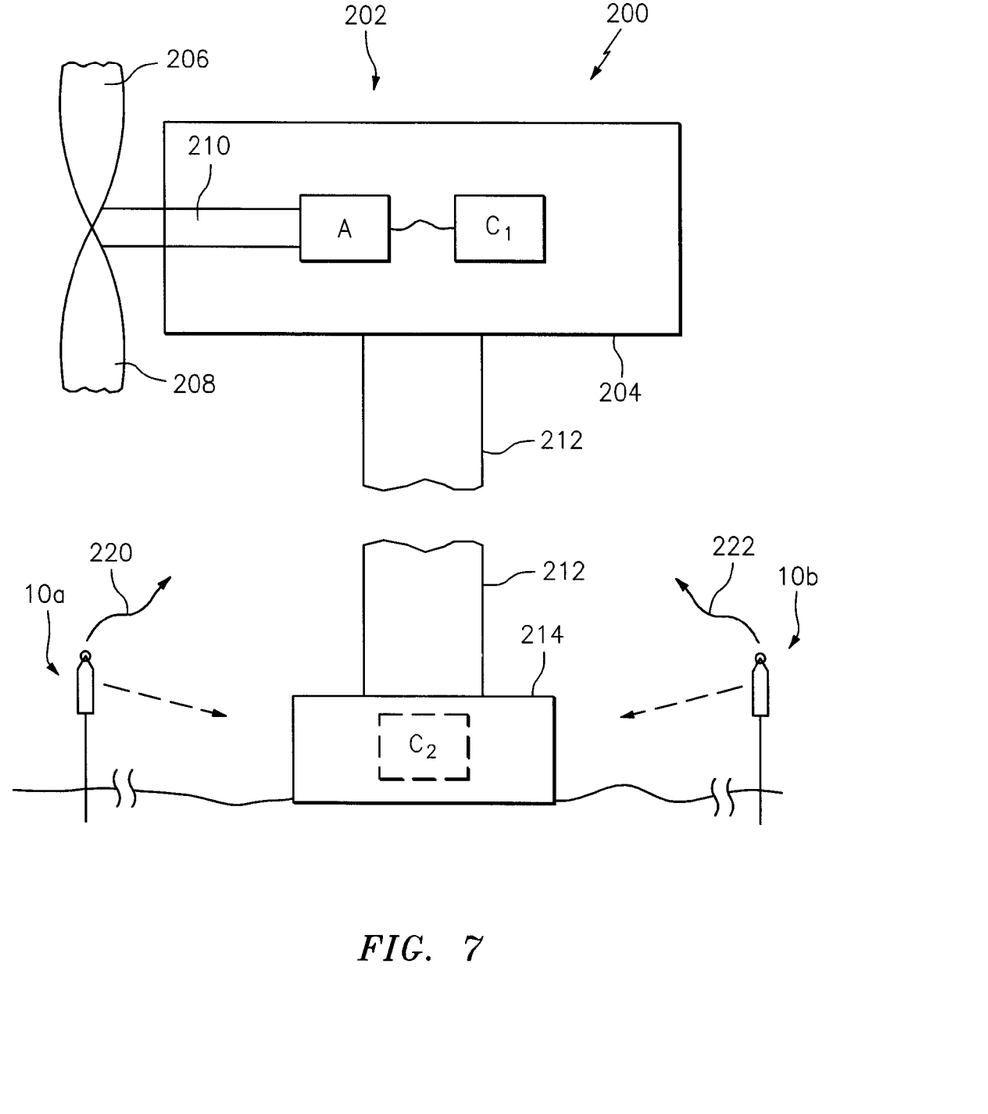
FIG. 7 is a schematic block diagram of a monitor and control system according to the present invention.

In addition to monitoring multiple emission modes, a monitor and control system 200 according to the present invention is shown in FIG. 7 providing control for a wind turbine 202 having a nacelle 204 and blades 206 and 208 connected to a drive shaft 210 extending into nacelle 204, which is supported by tower 212 mounted on a base 214. In this construction, system 200 includes a least two sensor arrays 10a and 10b which transmit data signals 220 and 222 to a controller $C_1$ within nacelle 204. In another construction, a controller $C_2$ is positioned in tower 212 or in base 214, as shown in dashed lines. The controller $C_1$ and/or $C_2$ analyzes at least multi-modal signals 220 and 222. When at least one parameter exceeds a pre-determined range of acceptable values beyond a specified period of time, the controller commands actuator A to alter at least one operation parameter such as changing the speed of rotation of blades 206, 208 and/or altering the pitch of the blades 206, 208. Feedback from subsequent multi-modal sensor readings is utilized by the controller to confirm that undesirable emissions have been properly mitigated.

Example 4

In one embodiment a multimodal invention is fabricated with at least the following specifications:

| | |
|---|---|
| Dimensions, Sensor head | 3 inches diameter by 10 inches tall |
| Dimension Erected | 1.5 meters to top of sensor head |
| Power requirements, Stand Alone pack | 4 weeks on rechargeable 7.2 V Li—Po battery |
| Power requirements | 12 V/100 mA supply or Power Over Ethernet option |
| Sensors | |
| light: | 2 pi1 radiative, 4 pi scalar, and off axis reference sampled at 40 Hz |
| audible acoustics: | 20 to 22,000 Hz, ⅓ Octave spectrum analysis |
| infrasound: | 0.1 to 20 Hz, Barometric compensated |
| E/M field | Steady state to 120 Hz |
| Ground vibration | |
| Output | Fixed field ASCII output |
| Data Format | Selectable to meet user needs |
| Onboard Storage | 8 GB using SD Card, PC formatted files |
| Calibration | Optional field calibration source |
| Installation requirements/assembly | Level and post hole digger (change this language) |
| Operating temperature range | 25 to 115 degrees F. |

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. The utilities thereof can be appreciated by those skilled in the art. It should be emphasized that the above-described embodiments of the present invention merely describe certain examples implementing the invention, including the best mode, in order to set forth a clear understanding of the principles of the invention. All variations and modifications, including equivalents thereof, are intended to be included within the scope of the present invention, as set forth herein.

It is the intention, therefore, to be limited only as indicated by the scope of the claims appended hereto. Other embodiments will occur to those skilled in the art and are within the following claims.

What is claimed is:

1. A multi-modal environmental monitor, comprising:
a first sensor for measuring at least one type of electromagnetic emission and generating a first emission signal;
a second sensor for measuring at least one type of mechanical wave emission and generating a second emission signal;
at least one clock to synchronize the first and second emission signals;
at least one data storage unit capable of storing the first and second emission signals over time; and
a housing containing at least the first and second sensors and capable of being placed operationally in an outdoor location to be monitored, wherein the first sensor measures at least one type of optical radiation, further including a third sensor for measuring a different type of optical radiation, and wherein one of the first and third sensors is a steradian scalar collector and the other of the first and third sensors is an irradiance collector.

2. The monitor of claim 1 wherein the second sensor measures at least one of audible sound and infrasound.

3. The monitor of claim 2 further including a ground-coupled vibration sensor.

4. The monitor of claim 1 further including a sensor to detect an electromagnetic field emitted from a human-made source.

5. A multi-modal monitor system to obtain quantitative, coordinated measurement of emissions from a designated outdoor source, comprising:
- at least two sensor arrays, each array including a first sensor for measuring at least one type of electromagnetic emission and generating a first emission signal, and a second sensor for measuring at least one type of mechanical wave emission and generating a second emission signal, the first and second sensors contained within a housing capable of being placed operationally in an outdoor location to be monitored;
- a controller which compares the emission signals with pre-determined ranges of acceptable values and alters the performance of the designated outdoor source when at least one parameter deviates from the pre-determined range of acceptable values for at least a specified period of time;
- at least one clock to synchronize the first and second emission signals from each array; and
- at least one data storage unit capable of storing the first and second emission signals from each array over time.

6. The monitor system of claim 5 wherein the first sensor in each array measures at least one type of optical radiation.

7. The monitor system of claim 6 wherein each array further includes a third sensor for measuring a different type of optical radiation.

8. The monitor system of claim 7 wherein one of the first and third sensors in each array is a steradian scalar collector and the other of the first and third sensors is an irradiance collector.

9. The monitor system of claim 8 wherein the second sensor in each array measures at least one of audible sound and infrasound.

10. The monitor system of claim 9 wherein each array further includes a ground-coupled vibration sensor.

11. The monitor system of claim 10 wherein each array further includes a sensor to detect an electromagnetic field emitted from a human-made source.

12. A multi-modal environmental monitor, comprising:
- a first sensor for measuring at least one type of electromagnetic emission and generating a first emission signal, wherein the first sensor measures at least one type of optical radiation;
- a second sensor for measuring at least one type of mechanical wave emission and generating a second emission signal;
- a third sensor for measuring a different type of optical radiation, wherein one of the first and third sensors is a steradian scalar collector and the other of the first and third sensors is an irradiance collector;
- at least one data storage unit capable of storing the first and second emission signals over time; and
- a housing containing at least the first and second sensors and capable of being placed operationally in an outdoor location to be monitored.

* * * * *